United States Patent
Cvetovich (12)

(10) Patent No.: US 6,350,915 B1
(45) Date of Patent: *Feb. 26, 2002

(54) PROCESS FOR THE SYNTHESIS OF 1-(3,5-BIS(TRIFLUOROMETHYL)-PHENYL) ETHAN-1-ONE

(75) Inventor: Raymond Cvetovich, Scotch Plains, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/590,426

(22) Filed: Jun. 8, 2000

Related U.S. Application Data

(60) Provisional application No. 60/138,735, filed on Jun. 11, 1999.

(51) Int. Cl.[7] ............................................. C07C 45/00
(52) U.S. Cl. ...................................................... 568/319
(58) Field of Search ........................................ 568/319

(56) References Cited

U.S. PATENT DOCUMENTS 5,235,068 A * 8/1993 Minai et al. ................. 548/540

FOREIGN PATENT DOCUMENTS

| JP | 967297 | 3/1997 |
| JP | 9169673 | 6/1997 |

OTHER PUBLICATIONS

Boudin, et al., *Tetrahedron*, 45 (1), 171–180 (1989).
Posner, et al., *Tetrahedron Letters*, No. 53, 4647–4650 (1970).
Stillings, et al., *J. Medicinal Chem.*, 29, 2280–2284 (1986).

* cited by examiner

*Primary Examiner*—Joseph K. McKane
*Assistant Examiner*—Joseph Murray
(74) *Attorney, Agent, or Firm*—J. Eric Thies; David L. Rose

(57) ABSTRACT

The present invention is concerned with a novel process for the preparation of 1-(3,5-bis(trifluromethyl)phenyl)ethan-1-one (CAS 30071-93-3). This compound is useful as an intermediate in the synthesis of therapeutic agents.

26 Claims, No Drawings

PROCESS FOR THE SYNTHESIS OF 1-(3,5-BIS(TRIFLUOROMETHYL)-PHENYL)ETHAN-1-ONE

CROSS REFERENCE TO RELATED APPLICATIONS

This application claims priority under 35 U.S.C. §119(e) from Ser. No. 60/138,735, filed Jun. 11, 1999.

BACKGROUND OF THE INVENTION

The present invention relates to processes for the preparation of 1-(3,5-bis(trifluoromethyl)phenyl)ethan-1-one (CAS 30071-93-3) which is useful as an intermediate in the preparation of therapeutic agents. In particular, the present invention provides a process for the preparation of 1-(3,5-bis(trifluoromethyl)-phenyl)ethan-1-one which is an intermediate in the synthesis of pharmaceutical compounds which are substance P (neurokinin-1) receptor antagonists.

The preparation of 1-(3,5-bis(trifluoromethyl)phenyl) ethan-1-one from 3,5-bis(trifluoromethyl)benzoyl chloride has been reported by Posner, G. H.; Whitten, C. E. *Tetrahedron. Lett.*, 4647 (1970). The disclosed process involves the addition of dimethyl copper lithium to 3,5-bis (trifluoromethyl)benzoyl chloride in an ethereal solvent. However, this reference requires multiple steps to obtain 1-(3,5-bis(trifluoro-methyl)phenyl)ethan-1-one from 3,5-bis (trifluoromethyl)bromobenzene, and a much more efficient and cost-effective process to 1-(3,5-bis(trifluoromethyl) phenyl)ethan-1-one would be highly desirable.

The general processes disclosed in the art for the preparation of 1-(3,5-bis(trifluoromethyl)phenyl)ethan-1-one result in relatively low and inconsistent yields of the desired product. In contrast to the previously known processes, the present invention provides effective methodology for the preparation of 1-(3,5-bis(trifluoro-methyl)phenyl)ethan-1-one in relatively high yield.

It will be appreciated that 1-(3,5-bis(trifluoromethyl) phenyl)ethan-1-one is an important intermediate for a particularly useful class of therapeutic agents. As such, there is a need for the development of a process for the preparation of 1-(3,5-bis(trifluoromethyl)phenyl)ethan-1-one which is readily amenable to scale-up, uses cost-effective and readily available reagents and which is therefore capable of practical application to large scale manufacture.

Accordingly, the subject invention provides a process for the preparation of 1-(3,5-bis(trifluoromethyl)phenyl)ethan-1-one via a very simple, short and highly efficient synthesis.

SUMMARY OF THE INVENTION

The novel process of this invention involves the synthesis of 1-(3,5-bis(trifluoromethyl)phenyl)ethan-1-one. In particular, the present invention is concerned with novel processes for the preparation of a compound of the formula:

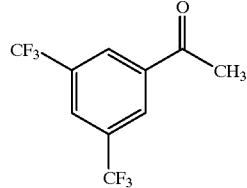

This compound is an intermediate in the synthesis of compounds which possess pharmacological activity. In particular, such compounds are substance P(neurokinin-1) receptor antagonists which are useful e.g., in the treatment of inflammatory diseases, psychiatric disorders, and emesis.

DETAILED DESCRIPTION OF THE INVENTION

The present invention is directed to processes for the preparation of 1-(3,5-bis(trifluoromethyl)phenyl)ethan-1-one of the formula:

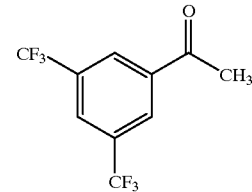

A preferred embodiment of the general process for the preparation of 3,5-bis(trifluoromethyl)-benzoic acid is as follows:

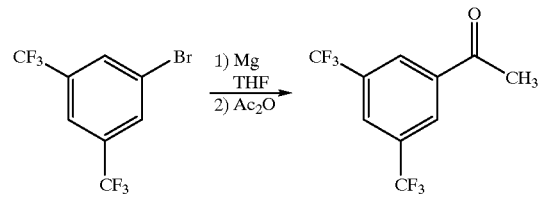

In accordance with the present invention, the treatment of acetic anhydride with the Grignard reagent from 3,5-bis (trifluoromethyl)bromobenzene provides 1-(3,5-bis(trifluoromethyl)phenyl)ethan-1-one in higher yields and in a more efficient route than the processes disclosed in the art.

In a preferred embodiment, the present invention is directed to a process for the preparation of 1-(3,5-bis (trifluoromethyl)phenyl)ethan-1-one which comprises the reaction of 3,5-bis(trifluoromethyl)bromobenzene with magnesium in THF to form a Grignard reagent followed by addition of the Grignard reagent to acetic anhydride to give 1-(3,5-bis(trifluoromethyl)phenyl)ethan-1-one.

A specific embodiment of the present invention concerns a process for the preparation of 1-(3,5-bis(trifluoromethyl) phenyl)ethan-1-one of the formula:

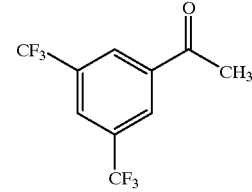

which comprises:

a) treating 3,5-bis(trifluoromethyl)benzene of the formula:

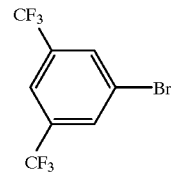

with magnesium in an organic solvent to form a Grignard reagent of the formula:

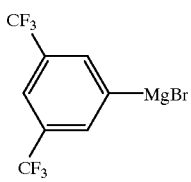

b) followed by contacting the Grignard reagent with acetic anhydride in an organic solvent to give 1-(3,5-bis(trifluoromethyl)phenyl)-ethan-1-one of the formula:

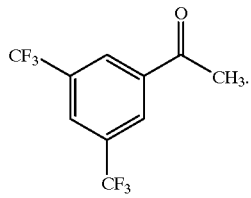

In the present invention it is preferred that the Grignard reagent is added to the acetic anhydride.

In a more preferred embodiment, following step (b) excess acetic anhydride is removed by the addition of an aqeueous solution of a base, such as sodium hydroxide, sodium bicarbonate, sodium carbonate, potassium hydroxide, and the like.

Preferred solvents for conducting the instant process comprise an organic solvent which is selected from toluene, tetrahydrofuran (THF), diethyl ether, diglyme, and methyl t-butyl ether. The most preferred organic solvent is tetrahydrofuran. In the formation of the Grignard reagent, tetrahydrofuran or diethyl ether are the more preferred organic solvents and tetrahydrofuran is the most preferred organic solvent.

The magnesium employed to prepare the Grignard reagent may be in the form of magnesium granules, magnseium turnings, magnesium dust, magnesium powder, suspension of magnesium in oil, and the like. To mimimize safety risks, the use of magnesium granules is preferred.

Grignard formation from 3,5-bis(trifluoromethyl) bromobenzene under typical conditions using magnesium turnings (4 equiv.) labeled as "suitable for Grignard reactions", diethyl ether solvent, and slow addition of the starting bromide resulted in facile formation of Grignard adduct (1–2 hours).

The use of less than 2.1 eq of magnesium turnings resulted in incomplete consumption of bromide (residual bromide >2–3 A%), while the use of more than 2.1 eq of magnesium turnings offered no advantage. A comparison of magnesium dust (freshly prepared), powder (50 mesh) and granules (20 mesh) showed that the Grignard reaction was complete for all within 1–2 hours at reflux in THF. The use of one type of magnesium over another offered no advantage in terms of reaction profile, purity, or yield of the desired product. The use of magnesium granules is preferred, however, because magnesium granules present less of a safety hazard.

The Grignard formation may be performed in tetrahydrofuran at reflux. The reaction is exothermic and the reaction may be controlled by the rate of addition of the bromide to the magnesium slurry. The reaction mixture may be aged at reflux until <1 mol % of bromide remains. Grignard formation is usually complete within 2 hours, however reaction times of up to 5 hours give comparable yields of 1-(3,5-bis (trifluoromethyl)phenyl)ethan-1-one.

To minimize solvent loss, however, the Grignard formation may be performed in tetrahydrofuran at a temperature range between about 0 and 20° C., and preferably a reaction temperature range between about 0 and 10° C.

In the present invention, it is preferred that the Grignard reagent be added to the acetic anhydride. In the present invention, it is also preferred that an excess of acetic anhydride be present when reacting the Grignard reagent. In the present invention, it is more preferred that the Grignard reagent be added to an excess of acetic anhydride.

Surprisingly, the presence of an excess of acetic anhydride (i.e. greater than a 1:1 molar ratio) is important to providing high yields of the desired product. When the acetic anhydride was added to the Grignard reagent at 20° C. an exothermic reaction resulted which produced a bis-adduct of the formula:

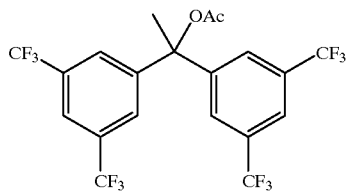

Surprisingly, however, when the Grignard reagent was added to acetic anhydride, little byproduct was formed and 1-(3,5-bis(trifluoromethyl)phenyl)ethan-1-one was obtained in 85–90% yield.

In the present invention, it is preferred that the Grignard reagent is added to cooled acetic anhydride In the present invention, it is more preferred that the Grignard reagent is added slowly (over a period of 1–2 hr, for example) to a cooled mixture of acetic anhydride in either tetrahydrofuran or tert-butyl methylether, maintaining the temperature at −10 to −15° C.

In the addition of the Grignard reagent with acetic anhydride, it is preferred that the temperature of the acetic anhydride upon addition of the Grignard reagent be less than about 0° C., more preferrably, less than about −10° C., it is even more preferrably less than about −15° C. Upon addition of the Grignard reagent, the temperature of the reaction mixture may be raised to about 10° C.

In a preferred additional embodiment, isolation of 1-(3, 5-bis(trifluoro-methyl)phenyl)ethan-1-one may be achieved by adding cold water to the reaction mixture followed by the slow addition of aqueous solution of a base to hydrolyze the excess acetic anhydride. The base may be an inorganic base selected from sodium hydroxide, potassium hydroxide, sodium bicarbonate, potassium carbonate, and the like. A preferred base is sodium hydroxide. The pH of the aqueous layer is preferably controlled at 8 to 8.5 at 10–20° C. When the pH maintained itself at 8.5 after a 15 min age, the mixture is extracted with tert-butyl methylether. The extracts are washed with aqueous sodium bicarbonate and aqueous sodium chloride and the solvents were removed by distillation.

The 1-(3,5-bis(trifluoromethyl)phenyl)ethan-1-one obtained in accordance with the present invention may be used as starting material in further reactions directly or following distillation. The isolated product can be distilled at atmospheric pressure to provide a clear colorless oil with BP=185–189° C.

Many of the starting materials are either commercially available or known in the literature and others can be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1
3,5-Bis(trifluoromethyl)bromobenzene

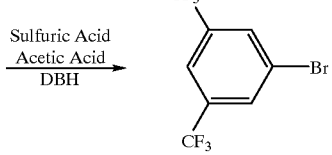

| Materials | MW | Density | Amount | Mmol | Equiv. |
|---|---|---|---|---|---|
| 1,3-Bis(trifluoro-methyl)benzene | 214.1 | 1.38 | 107 g | 500 | 1.0 |
| 96% H$_2$SO$_4$ | | | 142 mL | | |
| Glacial HOAc | | | 22 mL | | |
| 1,3-Dibromo-5,5-dimethylhydantoin | 285.93 | | 77.25 g | 270 | 1.08 (Br$^+$) |
| 5N Aq NaOH | | | 75 mL | | |

To glacial acetic acid (22.0 mL), cooled to 15° C. in a 1 L 3-n RB flask (equipped with mechanical stirrer, thermocouple, and addition funnel), was added concentrated (96%) sulfuric acid (142 mL) in one portion. An exothermic heat of solution raised the temperature to 35° C. After cooling to 25° C., 1,3-bis(trifluoro-methyl)benzene (107 g, 500 mmol) was added. With the acid mixture rapidly stirring, 1,3-dibromo-5,5-dimethylhydantoin (77.25 g; 270 mmol) was added over 2 min to give a multiple phase mixture (solid and two liquid). An exothermic reaction occured that raised the internal temperature to ~40° C. (jacket cooling at 15° C.). After the reaction temperature began to drop (after 5 min) the reaction mixture was maintained at 45° C. for 4.5 hr.

The rate and selectivity of the bromination is highly dependent on the agitation of the two phase reaction. Slower stirring increases the amount of bis-bromination and slows the overall rate of reaction. The reaction mixture remains heterogeneous throughout the reaction and the organic phase separates when agitation is interrupted. At the end of the reaction, the phases separate slowly (bromide density= 1.699). The rate of bromination is also dependent on the ratio of acetic to sulfuric acid.

Progress of the reaction is monitored by GC analysis, as follows.
Sample: ~50 μl of mixed phase, dilute with cyclohexane (1.5 mL), wash with water (1 mL), then 2N NaOH (1 mL), separate and inject.
Resteck RTX-1701 [60 meter×0.320 mm]: 100° C.; ramp: 5° C./min to 200° C.; 200° C. for 10 min; Flow 1.15 mL/min R$_t$: 1,3-bis(trifluoromethyl)benzene: 7.0 min
3,5-bis(trifluoromethyl)bromobenzene: 9.4 min
Biaryl: 19.2 min The mixture was cooled to 2° C. and poured slowly into cold water (250 mL). The mixture was stirred vigorously for 10 min, allowed to settle, and the lower organic layer was separated and washed with 5N NaOH (75 mL) to give 145.1 g of a clear, colorless organic layer.

The assay yield of 1,3-bis(trifluoromethyl)bromobenzene was 93.7% (137.3 g, 469 mmol), which contained 0.6% 1,3-bis(trifluoromethyl)benzene, 1.0% 1,2-dibromo-3,5-bis(trifluoromethyl)benzene, and 0.3% 1,4-dibromo-3,5-bis(trifluoromethyl)benzene. Total isomer byproducts measured by GC were 2.0 mol %.

EXAMPLE 2
1-(3,5-Bis(trifluoromethyl)phenyl)ethan-1-one

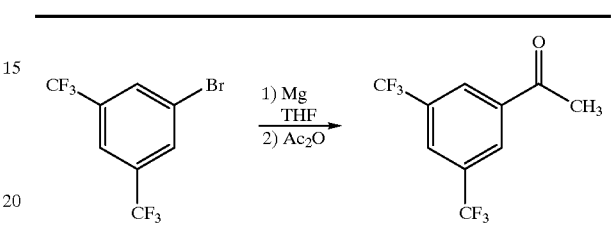

| Materials | MW | Density | Amount | Mmol | Equiv. |
|---|---|---|---|---|---|
| 1,3-Bis(trifluoro-methyl)-bromobenzene | 293.03 | 1.699 g/L | 29.3 g | 98.0 | 1.0 |
| Magnesium granules, 20 mesh | 24.3 | | 5.10 g | | 2.1 |
| Acetic Anhydride | 102.1 | 1.08 g/L | 40 mL | 423 | 4.5 |
| THF (KF = 60 μg/mL) | | | 260 mL | | |
| MTBE | | | 650 mL | | |
| Water | | | 300 mL | | |
| 50% NaOH | | | 40 mL | | |
| Product 3',5'-Bis(trifluoro-methyl)-acetophenone | 256.14 | | 20.3 g | 79.0 | 82% Yield |

To a 500 mL 3-neck round bottom flask equipped with an addition funnel, N$_2$ inlet, and a Teflon coated thermocouple was added magnesium granules (5.10 g, 210 mmol) and THF (200 mL). The mixture was heated to reflux. 3,5-Bis(trifluoromethyl)bromobenzene (29.3 g, 98 mmol) was dissolved in 30 mL of THF. Some bromide solution (5 mL) was added to the gently refluxing magnesium slurry over 2 minutes to initiate the Grignard reaction. After Grignard initiation, the remaining bromide was added over 1 hour. Alternatively, the Grignard initiation may be conducted at 0–20° C. to minimize the loss of solvent.

An initial induction period of 5 minutes is generally allowed for. If the reaction does not initiate, another 5% charge of bromide solution is added. If the reaction still does not initiate after a bromide charge of 10%, 100 mg of iodine is added. The reaction exotherm was controlled by slowing or stopping the bromide addition if the reaction appeared too violent.

After complete bromide addition (~60 minutes), the dark brown solution was heated at gentle reflux for an additional 30 minutes.

The reaction was monitored by HPLC (sample preparation: 100 μL sample quenched into 3.5 mL of 1:1 THF:2N HCl, then diluted to 100 mL in 65:35 acetonitrile:pH 6 buffer). Grignard formation was considered complete when the bromide level is less that 1 mol %.

After cooling to ambient temperature in a water bath, the mixture was transferred via cannula to a 1 L addition funnel. THF (10 mL) was used as rinse. This solution was then added to a solution of acetic anhydride (40 mL) in THF (40 mL) maintained at −15° C. over 1 hr. The dark brown mixture was warmned to 10° C. in a water bath, and water (300 mL) was added over 3 minutes. The biphasic mixture was vigorously stirred while 50% NaOH was added dropwise over 1 hr, until a pH of 8.0 was maintained for 5 minutes. MTBE (300 mL) was added, the layers were separated and the aqueous layer was further extraced with MTBE (3×150 mL). The organic layers were combined and assayed (22.4 g ketone), then concentrated in vacuo at bath temperature of 32° C. (50–80 torr). The concentrate was then distilled at atmospheric pressure and 20.7 g (82% yield based on LC purity) of colorless oil was collected at 150–189° C., with the bulk collected at 187–189° C.

| HPLC Assay: | 97.7 LCAP |
|---|---|
| Method: | Luna C18 |
| | Acetonitrile: 0.1% aq H$_3$PO$_4$ |
| | 75:25 to 95:5 over 20 min; maintain 5 min. |
| R$_t$ (min): | |
| Phenol | 5.2 |
| Ketone | 6.3 |
| Aromatic | 7.3 |
| Bromide | 9.7 |
| Dimer | 13.3 |
| GC Assay: | 95.5 GCAP |
| Method: | Resteck RTX-1701 [60 meter × 0.320 mm] |
| | 100° C. to 200° C. @ 5° C./min; 200° C. for 10 min; Flow 35 cm/sec constant flow. |
| R$_t$ (min): | |
| 1,3-bis(trifluoromethyl)benzene | 4.4 |
| Acetic anhydride | 5.6 |
| Methyl Ketone | 10.6 |
| 3,5-bis(trifluoromethyl)bromobenzene | 6.2 |
| Bis adduct | 19.6 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

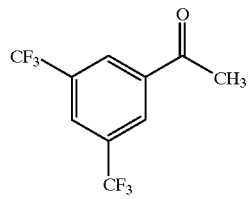

which comprises:

a) treating a compound of the formula:

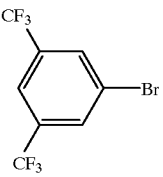

with magnesium in an organic solvent to form a Grignard reagent of the formula:

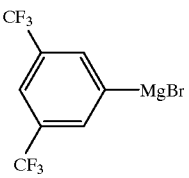

b) followed by contacting the Grignard reagent with acetic anhydride in an organic solvent to give the compound of the formula:

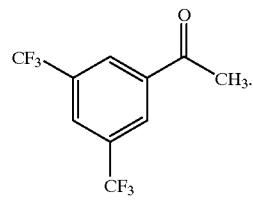

2. The process of claim 1 wherein the organic solvent comprises a solvent which is selected from: tetrahydrofuran, toluene, diethyl ether, diglyme, and methyl t-butyl ether.

3. The process of claim 1 wherein the organic solvent comprises tetrahydrofuran.

4. The process of claim 1 wherein the magnesium is in the form of magnesium granules, magnseium turnings, magnesium dust, magnesium powder, or a suspension of magnesium in oil.

5. The process of claim 1 wherein the magnesium is in the form of magnesium granules.

6. The process of claim 1 wherein the formation of the Grignard reagent is conducted at a temperature range between about 0 and 20° C.

7. The process of claim 1 wherein the Grignard reagent is added to acetic anhydride.

8. The process of claim 1 wherein the Grignard reagent is added to an excess of acetic anhydride.

9. The process of claim 1 wherein the temperature of the acetic anhydride upon addition of the Grignard reagent is less than about 0° C.

10. The process of claim 8 wherein the temperature of the acetic anhydride upon addition of the Grignard reagent is less than about −10° C.

11. The process of claim 9 wherein the temperature of the acetic anhydride upon addition of the Grignard reagent is less than about −15° C.

12. The process of claim 1 wherein following step (b), excess acetic anhydride is removed by the addition of an aqeueous solution of a base.

13. The process of claim 12 wherein following step (b), excess acetic anhydride is removed by the addition of an aqeueous solution of sodium hydroxide.

14. A process for the preparation of 1-(3,5-bis (trifluoromethyl)-phenyl)ethan-1-one which comprises the reaction of 3,5-bis(trifluoromethyl)-bromobenzene with magnesium in tetrahydrofuran to form a Grignard reagent followed by addition of the Grignard reagent to an excess of acetic anhydride to give 1-(3,5-bis(trifluoro-methyl)phenyl)ethan-1-one.

15. A process for the preparation of a compound of the formula:

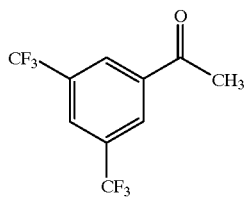

wherein comprises:

contacting a Grignard reagent of the formula:

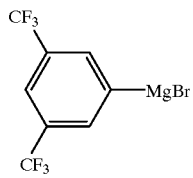

with acetic anhydride in an organic solvent to give the compound of the formula:

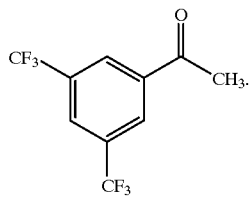

16. The process of claim 15 wherein the organic solvent comprises a solvent which is selected from: tetrahydrofuran, toluene, diethyl ether, diglyme, and methyl t-butyl ether.

17. The process of claim 15 wherein the organic solvent comprises tetrahydrofuran.

18. The process of claim 15 wherein the Grignard reagent is added to acetic anhydride.

19. The process of claim 15 wherein the Grignard reagent is added to an excess of acetic anhydride.

20. The process of claim 18 wherein the temperature of the acetic anhydride upon addition of the Grignard reagent is less than about 0° C.

21. The process of claim 19 wherein the temperature of the acetic anhydride upon addition of the Grignard reagent is less than about −10° C.

22. The process of claim 21 wherein the temperature of the acetic anhydride upon addition of the Grignard reagent is less than about −15° C.

23. The process of claim 15 wherein following contacting the Grignard reagent with acetic anhydride, excess acetic anhydride is removed by the addition of an aqeueous solution of a base.

24. The process of claim 23 wherein following contacting the Grignard reagent with acetic anhydride, excess acetic anhydride is removed by the addition of an aqeueous solution of sodium hydroxide.

25. A process for the preparation of 1-(3,5-bis(trifluoromethyl)- phenyl)ethan-1-one which comprises the reaction of 3,5-bis(trifluoromethyl)bromo- benzene Grignard reagent in an organic solvent with an excess of acetic anhydride to give 1-(3,5-bis(trifluoromethyl)phenyl)ethan-1-one.

26. The process of claim 25 wherein the organic solvent comprises tetrahydrofuran.

* * * * *